(12) United States Patent
Levi et al.

(10) Patent No.: US 6,413,506 B1
(45) Date of Patent: Jul. 2, 2002

(54) COMPOSITIONS FOR ELIMINATING HUMAN AND ANIMAL EXCREMENT SMELLS

(75) Inventors: Shalom Levi, Beer Sheva; Steve Daren, Nes Ziona, both of (IL)

(73) Assignee: Damar Holdings S.A., Nassau (BS)

( * ) Notice: Subject to any disclaimer, the term of this patent is extended or adjusted under 35 U.S.C. 154(b) by 0 days.

(21) Appl. No.: 09/341,237

(22) PCT Filed: Jan. 14, 1998

(86) PCT No.: PCT/IL98/00016

§ 371 (c)(1),
(2), (4) Date: Jul. 13, 1999

(87) PCT Pub. No.: WO98/30251

PCT Pub. Date: Jul. 16, 1998

(30) Foreign Application Priority Data

Jan. 14, 1997 (IL) .................................................. 120007

(51) Int. Cl.⁷ ........................... A61L 9/01; A61L 11/00; A61L 9/04
(52) U.S. Cl. .................... 424/76.1; 424/76.6; 424/76.4; 424/76.5; 424/76.9
(58) Field of Search ............................... 424/76.1, 76.6, 424/76.4, 76.5, 76.9

(56) References Cited

U.S. PATENT DOCUMENTS

| | | | | |
|---|---|---|---|---|
| 3,954,964 A | * | 5/1976 | Kuderna, Jr. ................. | 424/76 |
| 4,127,383 A | * | 11/1978 | Johnston et al. ................ | 422/5 |
| 4,405,354 A | * | 9/1983 | Thomas, II et al. ............ | 71/21 |
| 5,429,650 A | * | 7/1995 | Hoffmann et al. ............. | 55/224 |
| 5,456,701 A | * | 10/1995 | Stout ........................... | 607/104 |
| 5,882,638 A | * | 3/1999 | Dodd et al. ................... | 424/65 |
| 6,001,789 A | * | 12/1999 | Trinh et al. ................. | 510/191 |

FOREIGN PATENT DOCUMENTS

| | | |
|---|---|---|
| EP | 0 354 281 | 2/1990 |
| EP | 0354281 A1 * | 2/1990 |
| WO | 81 02891 | 10/1981 |

OTHER PUBLICATIONS

Abstract of JP 62 038 285.
Abstract of JP 06 165 815.
Abstract of JP 61 232 855.
Abstract of JP 61 137 565.
Abstract of JP 57 049 456.

* cited by examiner

Primary Examiner—Thurman K. Page
Assistant Examiner—S. Tran
(74) Attorney, Agent, or Firm—Lowe Hauptman Gilman & Berner, LLP

(57) ABSTRACT

The present invention relates to compositions (deodorizing or not) for human and animal excrement, especially pest and livestock, comprised of acidic agents and water soluble polymers, wherein the acidic agents are base neutralizers for the ammonia and indolic amines in the excrement and the water soluble polymers are barrier forming agents for the vapor of the offensive odor producing compounds in the excrement and for slowing down the air oxidative and enzymatic nitrification of the excrement ammonia and organic nitrogen thus dispersing and attenuating nitrate concentrations in the environment. The present invention further relates to a method of applying said compositions to excrement. Said compositions may be applied to excrement in liquid form by mixing the liquid composition together with the excrement, or in form of a spray, by spraying the composition directly on to the excrement.

2 Claims, No Drawings

COMPOSITIONS FOR ELIMINATING HUMAN AND ANIMAL EXCREMENT SMELLS

This application is a 371 of PCT/IL98/00016 filed Jan. 14, 1998.

FIELD OF THE INVENTION

The present invention relates generally to deodorant compositions for human and animal excrement and to a method for their use. The term "animal" as used in this specification refers especially to pets and livestock. More specifically the present invention relates to novel compositions, preferably aqueous compositions, comprises of acidic agents and water soluble polymers for applying on excrement, that are useful as deodorant compositions and for attenuating and dispersing nitrate concentrations in the environment and in the water reservoir, wherein the deodorizing of the excrement is based on acidification by organic acids and excrement coating by water soluble polymers which act as barriers for the offensive odor producing compounds of the excrement and form, upon drying, a film, turning the excrement into solid cakes easy to handle and with no perceptible odor.

BACKGROUND OF THE INVENTION

Owners of animals such as pets and livestock alike face problems caused by animal excrement; its foul odor and the need to eliminate it. Human excrement, such as in out houses in camp sites and army camps, pose the same problems. National and international regulations require that materials used for treating excrement, be non toxic and friendly to the environment, in particular that they do not contribute to adding nitrates or phosphates to the water reservoir. Additional requirements of commercial deodorizing compositions are low cost, simplicity of use in and outdoors and efficient deodorizing of excrement in liquid and solid forms. The principle targets of most existing treatment methods for preventing offensive odors of animal excrement, are ammonia and indolic amines. The common method to prevent offensive odors and retard bacterial and enzymatic decomposition is converting these compounds to their much less volatile ammonium salts by various organic and inorganic acids or their salts, as described in numerous publications.

Although acidification prevents offensive odors originating from basic ammonia and amines, it intensifies the offensive odors due to the excrement's volatile ammonium salts by various organic and inorganic acids or their salts, as described in numerous publications.

Although acidification prevents offensive odors originating from basic ammonia and amines, it intensifies the offensive odors due to the excrement's volatile organic acids such as acetic, propionic and butyric acids, due to the stabilization of their non ionized form. Furthermore, feces of low mobility do not come into full contact with the deodorizing agents which are usually absorbed or sprayed on pet's litter and hence are only partially deodorized. Therefore, these is a need for an inexpensive, effective and environment friendly composition which will include an impermeable barrier to excrement offensive odors in addition to safe deodorizing treatment of ammonia and idolic amines. This impermeable barrier has an additional advantage of slowing down the air oxidative and enzymatic nitrification of the excrement ammonia and organic nitrogen leading to dispersion and attenuation of nitrate concentrations in the environment. Of the known deodorizing formulations for pet and livestock few, if any, are of practical use. Use is made of cross-lined polymer gels, as water absorbing materials, in compositions for treatment of pet excrement, in several patents. Japanese patents 5,269,164, 3,290,126 and 2,238,834 disclose polymer gels with high water absorbing capacity for absorbing animal excretions. These gels may previously be blended with deodorant agents. Japanese patent 63185323 discloses absorbents for deodorizing pet excrement's. Polyvinyl alcohol is used as a binder in the production of pellets comprises of water absorbing inorganic polymers, like zeolites, and water soluble inorganic salts. U.S. Pat. No. 5,039,481 describes $NH_3$ scavenging deodorant made of aliphatic polycarboxylic acids for treatment of livestock excrement. Japanese patents 61119127 and 62153348 describe compositions for treating pet feces with a water insoluble coating to reduce odors and to enable feces to be removed by hand. These compositions, however, comprise toxic and ecologically unsafe volatile organic solvents such as acetone, methylene chloride, benzene, $CFCl_3$ and the expensive and toxic cyanoacrylic acid monomer.

The present invention describes novel deodorizing compositions comprising organic acids and water soluble polymers for excrement coating, which meet the above mentioned requirements. Furthermore, the present invention overcomes the two above mentioned major limitations of offensive odor due to stabilizing the non ionized form of excrement's volatile organic acids and low mobility feces not coming in full contact with the deodorizing composition, by incorporating water soluble barrier forming agents in the deodorant composition.

SUMMARY OF THE INVENTION

The present invention relates to deodorizing compositions for human and animal excrement, especially pets and livestock, comprised of acidic agents and water soluble polymers, wherein the acidic agents are base neutralizers for the ammonia and indolic amines in the excrement and the water soluble polymers are film forming polymers, of molecular weight higher then 15,000, forming a barrier [forming agents] for the vapor of the offensive odor producing compounds in the excrement. The present invention also relates to compositions (not necessarily deodorant compositions) comprised of acidic agents and water soluble polymers wherein the water soluble polymers are barrier forming agents useful for slowing down the air oxidative and enzymatic nitrification of the excrement ammonia and organic nitrogen thus dispersing and attenuating nitrate concentrations in the environment and in the water reservoir. These composition are preferably an aqueous solution. The present invention further relates to a method of applying said compositions to excrement. Said compositions may be applied to excrement in liquid form by mixing the liquid composition together with the excrement. This method is especially useful in treating livestock excrement. Said compositions may also be applied in form of a spray, by spraying the composition directly on to the excrement whereas, upon drying, the sprayed compositions form a thin film turning the excrement into solid cakes, easy to handle with no perceptible smell.

DETAILED DESCRIPTION OF THE INVENTION

The present invention relates to novel deodorizing compositions, preferably aqueous compositions, for human and animal excrement comprised of acidic agents and water soluble polymers, wherein the acidic agents are base neutralizers for the ammonia and indolic amines in the excrement and the water soluble polymers are barrier forming agents for the vapor of the offensive odor producing compounds in the excrement. When applied on excrement these compositions form, upon drying, thin film barriers which greatly reduce the vapor pressure of the offensive odor producing compounds and the intensified offensive odors due to the acidification which stabilizes the non ionized form of the excrement's volatile organic acids such as acetic, propionic and butyric acids. In the case of solid feces this film also traps the ammonia and indolic amines that may escape contact with the deodorizing agent. These compositions form, upon drying, a thin film turning the excrement into solid cakes, easy to handle with no perceptible smell. The acidic agents are preferably biodegradable organic acids or their soluble salts such as citric acid, glycolic acid, oxalic acid, polyacrylic acids, preferably in a concentration range of 1%–10%. The water soluble polymers are preferably hyroxyethyl cellulose, polyethylene oxide, polyvinyl pyrrolidone, polyhydroxyethyl (meth)acrylate, polyvinyl alcohol, polyhydroxypropyl (meth)acrylate, poly(meth)acrylamide, which are biologically degradable, non toxic and ecologically safe, preferably in a concentration range of 0.1%–10%. A fragrance, such as limonene, may be added to the compositions as natural fragrance. The water soluble coating polymers (WSCP) used in this invention are biodegradable, non toxic and friendly to the environment and can be included in various deodorizing compositions. The said invention will be further illustrated in detail by the following examples. These examples do not intend to limit the scope of the invention but to demonstrate and clarify it only. In the following examples WSCP were added to compositions based on aqueous solutions of carboxylic acids or combinations of carboxylic acids or their soluble salts. These compositions were applied to different animal excrements.

EXAMPLE 1 solution 1:5% (w/v) of polyvinyl alcohol (PVA) was obtained by dissolving 10 g of PVA (98% hydrolyzed, avg. M.W.=16,000) in 200 ml tap water (800 mho conductivity at 70° C. Composition 1.1 (2.5% PVA), a composition suitable for pets excrement was prepared from the following:

| solution 1 | 125 ml |
|---|---|
| water | 125 ml |
| citric acid | 12.5 g |
| monopotassium phosphate (MKP) | 12.5 g |
| limonene | 10 µl |

Composition 1.2 (1.5% PVA), a composition suitable for pets excrement and transported organic fertilizer, was prepared from the following:

| 1.5% PVA | 1000 ml |
|---|---|
| citric acid | 100 g |
| limonene | 20 µl |

Composition 1.1 was tested on cat litter in a family's home. 100 ml of composition 1.1 were sprayed on 2 kg of smelly cat litter, while slightly mixing the litter. Uncovered feces were occasionally sprayed lightly and brushed aside. A spraying bottle of 250 ml was used for two litter replacements in a three week period. During this time the excrement offensive smell was reduced significantly and replacement of the litter was needed only every 10 days as opposed to every 4 days, without treatment. On completion of the experiment with composition 1.1, composition 1.2 was tested on the same cat litter with similar deodorizing efficiency results.

EXAMPLE 2

This example shows a composition suitable both for pet excrement and for spraying on transported organic fertilizer.

Composition 2

| 1.5% polyvinyl alcohol aqueous solution | 100 ml |
|---|---|
| Citric acid | 5 g |

The citric acid was dissolved in 7 ml water and the solution was slowly added to the polyvinyl alcohol solution while stirring. 40 ml of this solution were mixed with 200 ml of pig excrement collected from a cesspit adjacent to the sty. The pH of the excrement was reduced from 7 to 6. 200 ml of a control (excrement with no addition) were placed in an open beaker about 10 m apart from the excrement treated with composition 2 in the open air.

After one hour in the sun a barrier film formed on the surface of the treated solution, preventing smell and protecting the underlying excrement from flies. The polyvinyl alcohol—citric acid solution was tested on cat litter as described in example 1. Similar results were obtained and the replacement of the litter was not required for 10 days after the initial spray.

EXAMPLE 3

This example shows the effect of acidification in an aqueous media, such as oxidation ponds and livestock excrement pools. Three samples of 20 liters of pig excrement, collected from a cesspit adjacent to the sty, were added to three 30 liter plastic tanks with a continuous air supply from air pumps. The three samples were treated with the following:

Composition 3.1

| 450 ml | glycolic acid (70%) |
|---|---|
| 107 ml | ethylene glycol |
| 300 g | ferrous sulfate heptahydrate |

Composition 3.2

| 450 ml | glycolic acid (70%) |
|---|---|
| 300 g | ferrous sulfate heptahydrate |

Control (no addition)

The initial pH of the excrement was 7.1 (measured using a glass electrode). Addition of compositions 3.1 and 3.2 brought the pH to 4.5 and 4.6 respectively. The tanks were allowed to stand outdoors for six months. The water lost due to evaporation was periodically replaced to maintain a constant volume.

After six months the following observations were made:

|  | composition 3.1 | composition 3.2 | control |
|---|---|---|---|
| pH | 5.92 | 6.12 | 6.77 |
| color | brown | brown | black |
| smell | moderate | moderate | foul |
| fly maggots | none | none | several |

EXAMPLE 4

This example demonstrates the effect of the polymers as barrier forming agents. The water was decanted from the three tanks from example 2 (after 6 months) and the following solutions were added to about 5 liters of the residual sludge:

to 3.1 450 ml of a 10% polyvinyl pyrrolidone solution.

to 3.2 260 mo of an 8% polyethylene oxide solution. the tanks were left in the sun for a week and the sludge dried out. Sample 3.2 dried into a solid cake which could easily be handled and had no perceptible smell. Sample 3.1 dried into a less strong cake and had a slight residual smell. The control sample was dispersed and had a residual smell, but less than when it was mixed with water.

EXAMPLE 5

This example shows the effect of polyvinyl pyrrolidone as a barrier forming agent in cat litter. A solution of 15 g of citric acid in 200 ml of water was added to 200 ml of a 2% solution of polyvinyl pyrrolidone with stirring. The pH of the solution formed by mixing was about 1.5. This mixture solution was sprayed on cat litter as described in example 1.

The excrement offensive smell was significantly reduced and replacement of the litter was needed only every 10 days as opposed to every 4 days, without treatment.

What is claimed is:

1. A method of deodorizing human and animal excrement, comprising the steps of:

spraying an aqueous deodorizing composition on said excrement, said aqueous deodorizing composition consisting essentially of one or more carboxylic acids in an amount sufficient to neutralize nitrogenous odor-generating components in said excrement, and water soluble film forming polymers in quantities sufficient to form a solid film over the bulk of said excrement; and allowing the aqueous deodorizing composition to dry until the water soluble film forming polymers form the solid film over the bulk of said excrement, thereby greatly reducing a vapor pressure of offensive odor producing compounds and facilitating easy handling of said deodorized excrement.

2. A method of deodorizing excrement of at least one of livestock, animal and human, comprising the steps of:

mixing an aqueous deodorizing composition with said excrement, said aqueous deodorizing composition consisting essentially of one or more carboxylic acids in an amount sufficient to neutralize nitrogenous odor-generating components in said excrement, and water soluble film forming polymers in quantities sufficient to form a solid film over the bulk of said excrement; and allowing the aqueous deodorizing composition to dry until the water soluble film forming polymers form the solid film over the bulk of said excrement, thereby blocking volatile odor-generating components and facilitating easy handling of said deodorized excrement.

* * * * *